US009441190B2

(12) United States Patent
Henderson et al.

(10) Patent No.: US 9,441,190 B2
(45) Date of Patent: Sep. 13, 2016

(54) COMPOSITION AND METHOD FOR TREATING WATER SYSTEMS

(71) Applicant: NCH Corporation, Irving, TX (US)

(72) Inventors: Ecaterina Henderson, Dallas, TX (US); Pedro G. Gomez, Euless, TX (US); John T. Buxton, Flower Mound, TX (US); Lyle H. Steimel, Flower Mound, TX (US)

(73) Assignee: NCH CORPORATION, Irving, TX (US)

( * ) Notice: Subject to any disclaimer, the term of this patent is extended or adjusted under 35 U.S.C. 154(b) by 0 days.

(21) Appl. No.: 14/532,639

(22) Filed: Nov. 4, 2014

(65) Prior Publication Data

US 2015/0125544 A1    May 7, 2015

Related U.S. Application Data

(63) Continuation-in-part of application No. 14/073,705, filed on Nov. 6, 2013.

(60) Provisional application No. 62/010,042, filed on Jun. 10, 2014.

(51) Int. Cl.
  *C11D 7/10* (2006.01)
  *C23F 11/08* (2006.01)
  *C23F 14/02* (2006.01)
  *A01N 25/34* (2006.01)

(52) U.S. Cl.
  CPC ............... *C11D 7/10* (2013.01); *A01N 25/34* (2013.01); *C23F 11/08* (2013.01); *C23F 14/02* (2013.01)

(58) Field of Classification Search
  None
  See application file for complete search history.

(56) References Cited

U.S. PATENT DOCUMENTS

| | | |
|---|---|---|
| 1,674,827 A | 6/1928 | Fleming |
| 3,106,541 A | 10/1963 | Lipowski et al. |
| 3,173,864 A | 3/1965 | Freedman |
| 3,410,649 A | 11/1968 | Sellet |
| 3,428,557 A | 2/1969 | Rivers |
| 3,503,890 A | 3/1970 | Davisson et al. |
| 3,582,461 A | 6/1971 | Lipowski et al. |
| 4,005,009 A | 1/1977 | Kinoshita et al. |
| 4,306,967 A | 12/1981 | Trautwein |
| 4,383,077 A | 5/1983 | Bankert |
| 4,830,761 A | 5/1989 | Leach et al. |
| 4,931,187 A | 6/1990 | Derham et al. |
| 5,057,229 A | 10/1991 | Schulenburg et al. |
| 5,253,759 A | 10/1993 | Gouge et al. |
| 5,294,916 A | 3/1994 | Bolton et al. |
| 5,576,481 A | 11/1996 | Beardwood |
| 5,874,026 A | 2/1999 | Pilsits, Jr. et al. |
| 6,040,406 A * | 3/2000 | Carrier et al. ............ 526/238.22 |
| 6,063,290 A | 5/2000 | Failon et al. |
| 6,149,821 A | 11/2000 | Rounds et al. |
| 6,149,822 A | 11/2000 | Fabri et al. |
| 6,183,649 B1 | 2/2001 | Fontana |
| 6,346,275 B1 | 2/2002 | Auchincloss |
| 6,498,137 B1 | 12/2002 | Schalitz et al. |
| 6,701,940 B2 | 3/2004 | Tsibouklis et al. |
| 6,746,609 B2 | 6/2004 | Stander |
| 6,797,197 B2 | 9/2004 | Steimel et al. |
| 6,840,251 B2 | 1/2005 | Gill et al. |
| 7,141,174 B2 * | 11/2006 | Steimel et al. ............... 210/700 |
| 7,537,705 B2 | 5/2009 | Mizuno et al. |
| 7,632,412 B2 | 12/2009 | Johnson et al. |
| 7,959,943 B2 | 6/2011 | Hissong et al. |
| 7,976,873 B2 | 7/2011 | Myntti et al. |
| 7,993,675 B2 | 8/2011 | Oliver et al. |
| 2002/0185419 A1 | 12/2002 | Chandler |
| 2003/0094406 A1 | 5/2003 | Smith |
| 2003/0105072 A1 | 6/2003 | Degenhardt et al. |
| 2003/0108705 A1 | 6/2003 | Duffield et al. |
| 2005/0013878 A1 | 1/2005 | Mingzhong et al. |
| 2005/0040363 A1 | 2/2005 | Gray |
| 2007/0264296 A1 | 11/2007 | Myntti |
| 2008/0017337 A1 | 1/2008 | Duggirala et al. |
| 2008/0035580 A1 | 2/2008 | de Rijk |
| 2008/0169239 A1 | 7/2008 | Sparks et al. |
| 2009/0258086 A1 | 10/2009 | Myntti |
| 2010/0086576 A1 | 4/2010 | Myntti |
| 2010/0261631 A1 | 10/2010 | Isobe et al. |

(Continued)

FOREIGN PATENT DOCUMENTS

| | | |
|---|---|---|
| WO | WO2005021445 | 3/2005 |
| WO | WO2005051850 | 6/2005 |

OTHER PUBLICATIONS

M.A. Patrauchan et al., Calcium influences cellular and extracellular product formation during biofilm-associated growth of a marine *Pseudoalteromonas* sp., Journal, 2005, 13 pg.
Marigot Ltd. "GRAS Notification with respect to Phymatolithon calcareum and Lithothamnium corallioides" Jul. 1999.

*Primary Examiner* — Necholus Ogden, Jr.
(74) *Attorney, Agent, or Firm* — Ross Barnes LLP; Monty L. Ross; Robin L. Barnes

(57) ABSTRACT

A solid composition for treating cooling or heated water systems to remove scale, microorganisms and biofilm, and corrosion by-products. The composition for cooling towers and chilled water systems comprises chelating agents and an anionic surfactant. The composition for boilers and heated water systems comprises a sulfite, neutralizing amines, sodium phosphate, and, optionally, a polymethacrylate or polyacrylate polymer. A method for using such a treatment composition comprises contacting the treatment composition with substantially all parts of the water system.

21 Claims, No Drawings

(56) References Cited

U.S. PATENT DOCUMENTS

| | | |
|---|---|---|
| 2011/0008220 A1 | 1/2011 | Fleming et al. |
| 2011/0081713 A1 | 4/2011 | Fleming et al. |
| 2011/0293481 A1 | 12/2011 | Eanes et al. |
| 2012/0067793 A1 | 3/2012 | Ferrari et al. |
| 2012/0258156 A1 | 10/2012 | Rumberger et al. |
| 2013/0099158 A1 | 4/2013 | Moore et al. |
| 2013/0239991 A1 | 9/2013 | Denvir et al. |

* cited by examiner

COMPOSITION AND METHOD FOR TREATING WATER SYSTEMS

CROSS-REFERENCE TO RELATED APPLICATIONS

This application claims the benefit under 35 U.S.C. §119 (e) of U.S. Provisional Application Ser. No. 62/010,042 filed on Jun. 10, 2014. This application also claims the benefit under 35 U.S.C. §120 as a continuation-in-part of U.S. application Ser. No. 14/073,705 filed on Nov. 6, 2013.

BACKGROUND OF THE INVENTION

1. Field of the Invention

This invention relates to a solid treatment composition and method for treating water systems for scale, biofilm and microbial growth, and corrosion. This invention is particularly useful in anthropogenic cooling and chilled water applications, such as cooling towers, and boiler systems.

2. Description of Related Art

Anthropogenic water systems are critical components commonly found in most of the world's energy producing facilities, industrial and manufacturing plants, hospitals, and other institutional complexes and buildings. These systems consume around 700 billion gallons of water annually with a cost of $1.8 billion in sewage handling costs alone. All of these anthropogenic water systems require some form of treatment, either chemical or non-chemical, to control the build-up of scale, biofilm and other corrosion by-products on the important heat transfer surfaces that are necessary for efficient system operation.

For water systems involving heat exchange, such as cooling towers and boilers, effective treatment to remove these contaminants and to prolong the amount of time before the systems are re-contaminated can save significant amounts of money. An effective and thorough treatment may save costs for labor and treatment chemicals by reducing the frequency of periodic treatments or reducing the amount of chemicals needed for routine maintenance and/or periodic treatments. Such a treatment may also save on energy costs through the operation of clean heat exchange surfaces. Fouling of heat exchange surfaces costs U.S. industry hundreds of millions of dollars every year and is directly related to an increase in energy consumption of almost 3 quadrillion Btus (quads) annually.

To maximize the water usage and minimize waste, many of these systems employ a series of chemical treatments that protect the system against scaling, biofilm formation, and corrosion. For example the Chem-Aqua 15000 MTP product is one of the most common cooling tower chemical treatments, containing 2-phosphonobutane-1,2,4-tricarboxylic acid, and a series of high performance polymers to prevent calcium carbonate scale formation, azoles to inhibit copper corrosion and small amounts of molybdate for trace analysis. Chemical treatments such as the Chem-Aqua 15000 MTP product may be used with a number of non-oxidizing biocides including Bacticide 45 which is a 45% gluteraldehyde solution, Coolicide which is a 15% poly-quaternary ammonium solution, or a 1.5% Isothiazolin solution. In the larger industrial cooling tower systems and the cooling towers for coal and nuclear facilities it is more common to use sodium hypochlorite, 40% sodium bromide, or 11% bromine chloride liquid as the disinfectants.

These chemical treatments allow the water to be reused and recycled a number of times before it becomes necessary to discharge the water and replace it with fresh water. Increasing the duration for which the water may be circulated significantly reduces the amount of water that is discharged to the sewage system and minimizes the amount of make-up water that is needed to replace the bleed off. The chemical treatments also maintain the efficiency of the cooling tower and heat exchanger system. Many prior art treatment compositions and methods involve the use of liquid chemicals, typically shipped in large drums, which may make shipping and handling of the chemical compositions more difficult and expensive. Liquid treatments may be concentrated to reduce the volume of treatment product that must be shipped; however, the ingredients that may be useful in such treatment products are often not compatible in a concentrated liquid form, which limits the ability to use concentrated liquids. For example, certain surfactants, such as SugaQuats, will precipitate from solution rendering a concentrated liquid mixture inactive. Additionally, shipping and handling concentrated liquid treatment compositions can still be more costly and hazardous than if the treatment composition were in a solid form.

Additionally, many prior art treatment compositions and methods may damage the components of the water system being treated as the chemicals used are highly corrosive. There is also an environmental down side to the treatments. It is estimated that there are 536 billion pounds of water treatment chemicals discharged as a result of cooling tower treatments every year, which may impact a variety of species living in or near areas and water-ways receiving the discharge. Therefore it is desirable to use treatment chemicals that are considered less toxic. For example, citric acid and sodium citrate, which are both approved food additives, have been used in treatment compositions. The use of citric acid and sodium citrate, along with a cationic surfactant, is disclosed in Applicant's co-pending U.S. patent application Ser. No. 13/837,256.

Many prior art treatment compositions and methods require the use of strongly acidic, oxidizing, and toxic biocides for removal of biofilms. Biofilms contain mixed communities of bacteria including various species embedded in an exopolymer or "slime layer." As bacteria begin to attach to a surface, they secrete polymers, such as polysaccharides and glycoproteins called fibronectin. These allow the bacteria to adhere to a surface and form the conditioning layer of the biofilm. Once a confluent surface of sessile cells has formed, any other bacteria that contact this layer will be captured. Thus bound in this way, these bacterial cells begin to produce anchoring organelles and other compounds, allowing a secondary layer to form on top of the conditioning layer. As cells continue to attach and accumulate, underlying layers continue to reproduce and create a dense bacterial cluster. As these biofilm layers form they also accumulate other inorganic and organic debris that grow within the pipe restricting flow and causing blockages.

SUMMARY OF THE INVENTION

This invention relates to a solid chemical treatment composition and method for treating flowing or circulating water systems, such as a cooling tower, chilled water systems, and steam boilers.

A treatment composition according to one preferred embodiment of the invention, particularly useful in cooling tower and chilled water systems, comprises chemical chelating agents (organic or inorganic acids and their corresponding neutral salts) and an anionic surfactant. Although it may be used in other types of cooling and chilled water systems, this composition is referred to herein as the cooling tower composition. Citric acid and sodium citrate are preferred chelating agents and sodium diisopropyl naphthalene sulfonate is a preferred surfactant. It is preferred to form the composition as in a solid form, such as pellets, bricks, or powder.

Prior liquid treatment products required addition of three concentrated solutions. To treat 1,000 gallons of system water requires separate additions of about five gallons each of a mixed citrate solution and a surfactant solution, and system-based volume of a yellow metal inhibitor solution. With the liquid formulations, more than 100 pounds of additives are required to treat 1000 gallons. The liquid ingredients are also incompatible in concentrated form, and cannot be combined into one concentrate. The liquid products are not compatible due to limited water solubility in high electrolyte environments along with different pHs required for the raw materials to go into solution. The solid treatment composition according to the invention avoids the potential incompatibilities associated with concentrated liquid compositions. Additionally, the liquid composition may result in excess foaming, requiring the addition of an anti-foaming agent, which may be eliminated with a treatment composition in solid form according to the invention.

According to a preferred embodiment, the cooling tower treatment composition has concentrations of around 680 to 2700 ppm (or mg/L) neutral salt, 30 to 120 ppm acid salt, and 50 to 200 ppm anionic surfactant when added to the water of the system. One or more corrosion inhibitors, particularly copper inhibitors such as tolyltriazole ("TTA"), are also preferably used with the reagents in the treatment composition in concentrations around 1 to 20 ppm, and most preferably around 10 ppm, when added to the water of the system. A secondary biocide may also be added to or used with the treatment composition for controlling microorganisms and water parasites. Additional ingredients, such as magnesium stearate, may also be added to aid in formulation of a pelletized or brick form of the cooling tower treatment composition.

A treatment composition according to another preferred embodiment of the invention, particularly useful as a phosphate cycle treatment in steam boiler systems, comprises active reagents to function as oxygen scavengers. The treatment composition comprises a complex amine salt preferably made from cyclohexylamine, morpholine, monosodium phosphate and/or sodium metabisulfite and deionized water. Cyclohexylamine and/or morpholine (neutralizing amines) and a sulfite (preferably sodium sulfite or potassium sulfite) are used as oxygen scavengers and condensate treatment. Optionally, the complex amine salt may be further combined with a polymer, and sodium sulfite and disodium phosphate to form another preferred treatment composition (a two-part composition). These treatment compositions, either the complex amine salt alone or the two-part composition, are referred to herein as the boiler treatment composition, although it may be used in other heated water systems. In the two-part composition, a polymer (preferably sodium neutralized salt of polymethacrylate or polyacrylate) and sodium phosphate or potassium phosphate are used for hardness control. According to a preferred embodiment, the complex amine salt composition has concentrations of around 5 to 200 ppm total neutralizing amines, 5 to 100 ppm sodium sulfite, and 5 to 100 ppm phosphates when added to the water of the system. According to a preferred embodiment, the two-part boiler treatment composition has concentrations of around 0 to 200 ppm total neutralizing amines, 5 to 50 ppm polymer, 5 to 100 ppm sodium sulfite, and 5 to 100 ppm disodium phosphate when added to the water of the system. The monosodium phosphate and/or sodium metabisulfite from the first part of the treatment composition will dissociate in the water of the boiler system to form sodium sulfite and/or sodium phosphate, which are useful in treating the boiler system.

The boiler treatment composition is mixed and stored as a concentrated all-in-one solid formulation, preferably in pellets or a powder that is dissolved on site and added to the boiler water to provide effective treatment. The solid boiler treatment composition replaces prior liquid formulations, which usually required around five separate liquid products. The use of a solid treatment composition reduced shipping costs, eliminates handling of large and heavy liquid storage drums, eliminates flammable liquids, and reduces harsh amine odors. Additional ingredients, such as polyethylene glycol, may also be added to aid in formulation of a pelletized or brick form of the boiler treatment composition.

A method for treating water systems according to a preferred embodiment of the invention for a flowing water system comprises the steps of (1) bleeding or draining the water system and re-filling, as necessary, to remove the existing water and any previous water treatment compositions that may react with or otherwise interfere with the treatment composition; (2) determining the total volume of water in the system and re-filling the system with water; (3) adding a treatment composition so that the final concentrations of active reagents in the water system are greater than minimum concentrations of either cooling tower treatment composition or boiler treatment composition described herein; (4) circulating the water with the treatment composition throughout the system for a sufficient time; (5) optionally conducting periodic testing of the system for corrosion products to monitor the corrosive effects of the treatment composition on the water system; (6) optionally filtering the water to remove dislodged solids and biofilm agglomerates and monitoring the filter for necessary replacement as the treatment composition circulates through the water system; and (7) bleeding or draining the water containing the treatment composition from the water system after sufficient treatment time and removing any remaining solids in the sump or other water reservoir or low flow areas of the system, then refilling with fresh water.

As used herein, "fresh" water includes any source of water that is supplied to the water system from an available water source, such as a municipal water supply, a well, river, pond, or lake, or water recycled from another industrial process. Most typically, this water is from a municipal water supply. These methods result in a thorough cleaning of the water system, after which other, conventional water treatment regimens may be resumed and these methods utilized for periodic maintenance.

Most preferably, the concentrations of active reagents of the cooling tower treatment composition used with these preferred methods (when mixed with the water of the system) are concentrations of around 680 to 2700 ppm neutral salt, 30 to 120 ppm acid salt, and 50 to 200 ppm anionic surfactant. Higher concentrations may result in excessive corrosion in water systems having copper, mild steel and galvanized steel components. Most preferably, the solid cooling tower treatment composition includes a corrosion inhibitor, such as tolytriazole sodium salt. Separate or additional commercially available corrosion inhibitor(s) (particularly copper inhibitors if the water system has copper components) and biocides in amounts indicated on the product labels, may also be added along with the treatment composition. Most preferably, the concentrations of active reagents of the boiler treatment composition used with these preferred methods (when mixed with the water of the system) are around 0 to 200 ppm total neutralizing amines, 5 to 100 ppm polymer, 5 to 200 ppm sodium sulfite, and 5 to 100 ppm disodium phosphate when added to the water of the system. Higher concentrations may result in corrosion or scale deposition on the heat transfer surfaces or be cost prohibitive.

One advantage of the solid cooling tower compositions and methods of the invention is that they effectively remove biofilm and scale that are not effectively removed by conventional prior art treatment protocols. The treatment compositions improve overall treatment performance as a result of a synergistic interaction between the reagents of the compositions. The treatment compositions, preferably having reagents in solid form that are dissolved on site using the water in the system being treated or fresh water, also decreases the costs and risks associated with shipping and handling large volumes of liquid treatment chemicals. Additionally, the methods of the invention provide optimal cleaning while minimizing damage to the materials that make up the components of the water system being treated.

DESCRIPTION OF THE PREFERRED EMBODIMENTS

According to one preferred embodiment, a cooling tower treatment composition comprises chemical chelating agents (organic or inorganic acids and their corresponding neutral salts) and an anionic surfactant combined in solid form. These chelating agents aid in metal ion sequestration from any biofilm, hard scale, and bulk water present in the water system being treated. Most preferably, the acid is citric acid and the salt is sodium citrate. The surfactant is preferably an anionic surfactant, and most preferably a surfactant with antimicrobial properties. Preferred surfactants include sodium diisopropyl naphthalene sulfonate and didecyl dimethyl ammonium chloride (the quat, foaming). The surfactant aids in swelling and dissolving the extra cellular polysaccharide matrix that makes up a biofilm. In addition it can create an antimicrobial environment for microorganisms or water borne parasites that may be present in the water or biofilm environment. The use of a solid form for the cooling tower treatment composition allows for the use of a wider variety of surfactants without the problems associated with the surfactant precipitating out of solution or other incapabilities associated with concentrated liquid formulas.

The preferred cooling tower treatment composition comprises between about 65 to 90% neutral salt (such as sodium citrate), 1 to 6% acid (such as citric acid), and 6 to 15% anionic surfactant (such as sodium dissopropyl naphthalene sulfonate). It also preferably comprises about 0.1 to 1.5% corrosion inhibitor (such as tolytriazole sodium salt), 2 to 7% sodium bicarbonate (to aid in pelletization or other solid formation), and 0.25 to 0.75% magnesium stearate (to aid in pelletization or other solid formation), with these percentages being by weight. Most preferably, the cooling tower treatment composition comprises about 82% sodium citrate, 3.6% citric acid, 0.8% tolytriazole sodium salt (corrosion inhibitor), 8.1% sodium dissopropyl naphthalene sulfonate (surfactant), 5% sodium bicarbonate, and 0.5% magnesium stearate.

A similar concentrated liquid composition was tested in the lab and found to be unstable at room temperature (around 68° F.). A pelletized composition was tested at varying temperatures between 40° F. and 122° F. and was found to be stable. Around 12-14 pounds of pelletized cooling tower treatment composition are needed to treat 1000 gallons of water, compared to around 100 pounds of the similar separate liquid ingredients previously used. The pellets preferably weigh around 0.38 to around 0.43 grams each, are around 0.306 to 0.338 inches thick, and are around 1.5-2.2 Kp in hardness (top to bottom). The ingredients of the composition are mixed, preferably using a V-blender, and pelletized using a tablet press in a temperature and humidity controlled room. Those of ordinary skill in the art will understand how to make the treatment composition in solid form, such as bricks, pellets, or powder.

When the cooling tower treatment composition is added to the water system, the preferred concentrations of active agents in the total volume of water in the system are about 680 to 2700 ppm neutral salt, 30 to 120 ppm acid salt, 50 to 200 ppm surfactant. A corrosion inhibitor is also preferably used with the treatment product in an amount around 1-20 ppm, and most preferably around 10 ppm. The most preferred concentrations of a cooling tower treatment composition in the treated water are around 1350 ppm sodium citrate, 60 ppm citric acid, 100 ppm surfactant, 10 ppm corrosion inhibitor, 83 ppm sodium bicarbonate, and 8 ppm magnesium stearate. A preferred corrosion inhibitor is tolytriazole sodium salt and a preferred surfactant is sodium diisopropyl naphthalene sulfonate. Other treating agents, such as a secondary biocide, may also be added to the treatment composition or they may be separately added to the water system, either through a side stream or directly into the sump. However, unlike liquid formulations, it is not necessary to use an anti-foaming product with the cooling tower treatment composition.

According to another preferred embodiment, a boiler treatment composition comprises a dry complex amine salt, and, optionally, a polymer, a sulfite and a phosphate. The first part of the composition, the dry complex amine salt, preferably comprises around 2 to 70% (total) of one or more neutralizing amines, 2 to 70% by weight of a phosphate, 0 to 30% by weight of a sulfite, and 3 to 10% water. More preferably, the first part of the composition comprises around 20 to 30% cyclohexylamine (used as a neutralizing amine), 10 to 20% morpholine (used as a neutralizing amine agent), 30 to 40% sodium metabisulfite (used as an oxygen scavenger), 15 to 20% monosodium phosphate (used as a deposited conditioning agent) and 3 to 9% deionized water (a common solvent). Most preferably, the first part of the composition comprises around 30% sodium metabisulfite, 25% cyclohexylamine, 15% morpholine, 24% monosodium phosphate and 6% deionized water. The cyclohexylamine and or morpholine are in liquid form when added to the monosodium phosphate and or metabisulfite. In the presence of water, they react to form a dry complex amine salt. The cyclohexylamine, morpholine, and sulfite act as oxygen scavengers and condensate treatment agents in the boiler treatment composition. It is preferred to use both cyclohexylamine and morpholine, but either may be used without the other with adjustments to the weight percentages as will be understood by those of ordinary skill in the art. Additionally, diethylaminoethanol may also be used, alone or in combination with cyclohexylamine and/or morpholine as a neutralizing amine agent. Effective sulfites include sodium and potassium sulfite and sodium and potassium metabisulfite. Although referred to herein as the "first part" of the composition, this composition may be used alone as a boiler or other heated water system treatment or may be combined with other ingredients, including those discussed below as the "second part" of a two-part formula.

When used alone, the first part composition (the dry complex amine salt) preferably comprises around 1 to 70% of the neutralizing amine (used as an oxygen scavenger and deposit conditioning agent), 5 to 100% sodium sulfite (used as an oxygen scavenger agent), 1 to 100% disodium phosphate (used as a deposit conditioning agent), 2 to 6% polyethylene glycol (used as a tablet conditioning agent, if the composition is being formed into tablet or pellets, but this is not required for other formulations, such as a powder), and 3 to 9% water. The percentages herein are by weight. The actual amount of each chemical added to the boiler treatment composition will depend on the precise intended use concentrations (concentrations of the active ingredients in the total volume of water of the system being treated) and the concentration of each chemical when purchased and added to the treatment composition.

The amine salt mixture from the first part of the composition may, optionally, be added to second part ingredients, namely a polymer, sulfite, and phosphate (and other ingredients) to form a final two-part composition. The polymer and sodium phosphate or potassium phosphate are used for hardness control. The polymer is preferably the sodium neutralized salt of polymethacrylate or polyacrylate having a molecular weight of from 500 to 15,000, and used in 5-50 ppm concentrations. The polymethacrylates and polyacrylates can be obtained in a wide range of molecular weights, but generally the molecular weight should range from 500 to 15000 with 9000 being preferred. The most preferred is polymethacrylate with a molecular weight of about 9000. The final two-part composition preferably comprises around 50 to 60% of the amine salt from the first part (used as a neutralizing amine, oxygen scavenger and deposit conditioning agent), 5 to 15% sodium salt of polymethacrylic acid (used as a deposit control agent), 15 to 20% sodium sulfite (used as an oxygen scavenger agent), 8 to 15% disodium phosphate (used as a deposit conditioning agent), and 2 to 6% polyethylene glycol (used as a tablet conditioning agent). Most preferably, the final two-part boiler treatment composition comprises around 55% of the amine salt from the first part, 11% sodium salt of polymethacrylic acid, 18% sodium sulfite, and 12% disodium phosphate and is in a solid, preferably pelletized form. It also preferably comprises around 4% polyethylene glycol, which aids in pelletizing the formula. The percentages herein are by weight. The actual amount of each chemical added to the boiler treatment composition will depend on the precise intended use concentrations (concentrations of the active ingredients in the total volume of water of the system being treated) and the concentration of each chemical when purchased and added to the treatment composition.

The ingredients of the first part of the composition are mixed using a ribbon blender. The resulting amine salt may then be used, alone or combined with or in addition to other ingredients in treating a boiler or other heated water system. The resulting amine salt may be combined with the second part of the two-part formula using a ribbon blender to form the final two-part composition and pelletized using a tablet press in a temperature and humidity controlled room. Around 0.1 pounds of the first part solid treatment composition are needed to treat 1000 gallons of water, compared to 1.0 pounds of the similar separate liquid ingredients. Around 0.1 pounds of the two-part solid boiler treatment composition are needed to treat 1000 gallons of water, compared to around 1.0 pounds of the similar separate liquid ingredients previously used. If made into pellets, the pellets for either the first part formula or the two-part formula preferably weigh around 0.38 to 0.043 grams each, are around 0.306 to 0.338 inches thick, and are around 1.5 to 2.2 Kp in hardness (top to bottom). The ingredients of the composition are mixed, preferably using a V-blender, and pelletized using a tablet press in a temperature and humidity controlled room.

When the first part boiler treatment composition is added to the water system, it is preferred that it be added so that the concentrations of active agents are within certain ranges. The preferred ranges are about 5 to 200 ppm amine, 5 to 100 ppm sulfite, and 1 to 100 ppm phosphate, when added to the water of the system being treated. More preferably, the concentration ranges are as follows: The concentration of sodium or potassium sulfite is preferably from about 20 to about 40 ppm in the boiler. Since the sulfite is consumed during the treatment, the boiler treatment composition preferably contains a slight excess of sulfite, generally to give an initial concentration of about 20 to 100 ppm. Sufficient cyclohexamine and morpholine are provided to neutralize the acid and to provide a condensate pH of 7.5-8.5. To provide both condensate treatment and neutralization of the acid generally about 5 to about 200 ppm cyclohexamine and morpholine (combined total amount) are required. The concentration of cyclohexylamine and morpholine are preferably about 20 to 100 ppm total. Preferably, the concentration of potassium or sodium phosphate is about 10 to about 40 ppm in the boiler. Most preferably, the concentrations of the boiler treatment composition in the total volume of water in the boiler are about 2 to 100 ppm total amine, 20 to 40 ppm sulfite, and 10 to 40 ppm phosphate.

When the two-part boiler treatment composition is added to the water system, it is preferred that it be added so that the concentrations of active agents are within certain ranges. The preferred ranges are about 0 to 500 ppm amine, 5 to 100 ppm polymer, 5 to 200 ppm sulfite, and 5 to 100 ppm phosphate, when added to the water of the system being treated. More preferably, the concentration ranges are as follows: The concentration of sodium or potassium sulfite is preferably from about 20 to about 60 ppm in the boiler. Since the sulfite is consumed during the treatment, the boiler treatment composition preferably contains a slight excess of sulfite, generally to give an initial concentration of about 45 to 90 ppm. Sufficient cyclohexamine and morpholine are provided to neutralize the acid and to provide a condensate pH of 7.5-8.5. To provide both condensate treatment and neutralization of the acid generally about 1 to about 200 ppm cyclohexamine and morpholine (combined total amount) are required. The concentration of cyclohexylamine and morpholine are preferably about 10 to 50 ppm total. Preferably, the concentration of potassium or sodium phosphate is about 10 to about 60 ppm in the boiler. Preferably, the polymer concentration is about 1 to 80 ppm. Most preferably, the concentrations of the boiler treatment composition in the total volume of water in the boiler are about 10 to 50 ppm total amine, 30 to 60 ppm sulfite, 10 to 30 ppm phosphate, and 12-24 ppm polymer.

The treatment compositions may be fed directly into the water system being treated, such as in the sump of a cooling tower, or they may be fed using a solid product feeder, such as those described in U.S. Pat. No. 7,081,361, and published U.S. patent application Ser. Nos. 12/787,025, 12/498,793 and 12/571,714, which are incorporated herein by reference. The product feeder may feed solid treatment composition directly to the system to be treated or, more preferably, comprises a dissolution chamber for dissolving the treatment composition into a concentrated liquid and then feeding the concentrated into the system to be treated. When pre-dissolved, the dissolution chamber of the product feeder may be fed with fresh water or water from the system being treated that is diverted by a side stream, as will be understood by those of ordinary skill in the art. For example, the concentrated liquid treatment composition may be fed into the steam boiler, boiler feed water tank or deaerator. The use of a product feeder that pre-dissolves the treatment composition is preferred, since it gives the ease of mixing advantages of a liquid formula, but since it is created at the treatment site also gives the shipping and handling advantages of a solid formula.

For cooling tower systems, if the water in the system contains high levels of cationic species, there is the potential that the chelating agents will be consumed before they reach the reaction zone. Therefore to minimize parasitic reactions the system is preferably bled to a point where the conductivity of the water in the system is the same value as the water being used to make up water loss resulting from normal operation. After any necessary bleeding or draining of the system and re-filling with an appropriate volume of water, the treatment composition may be added to the water in the system. A corrosion rack/corrosion monitor and a conductivity meter to monitor the effectiveness of the treatment compositions and the level of corrosion caused by the treatment product on the components of the water system being treated are preferably used in conjunction with the treatment compositions. An in-line filtration mechanism to filter out biofilm agglomerates and other materials dislodged by the treatment compositions is also preferably used in conjunction with the treatment compositions. The cooling tower treatment composition preferably circulates through the water system for at least 4 hours, and may circulate as long as 24 hours.

As the water system circulates the treated water, the dissolved treatment composition begins to contact the contaminated surfaces. Calcium ions in the water form a thermoset polymer or bridging links that hold the extracellular polysaccharide matrix together, making biofilms difficult to dissolve and remove. The chelating agents attack any biofilm present on the surfaces and remove the bridging links. The surfactant and water penetrate the biofilm swelling it, which in turn enables penetration of the chelating reagents to further break apart the matrix. The neutral salt (preferably sodium citrate) used in the cooling tower treatment composition attacks the calcium bridges, allowing the anionic surfactant to penetrate and break-up the biofilm. Larger biofilm agglomerates may be sloughed off and enter the bulk water flowing through the system. As the water flows, these agglomerates are transported to other areas of the system where they can settle out (particularly in low flow areas, such as the sump) and become a secondary source of contamination. A filter may optionally be added to the water system to remove these biofilm agglomerates before they have a chance to reestablish colonies in the clean parts of the system. The filter should be monitored and replaced when it becomes fouled. This will be indicated by a visible soiling of the filter or by measuring an increase in pressure across the filter material. This helps prevent the filter material from becoming a secondary source of contamination that could result in further colonization of clean parts of the system. It is preferred that upon completion of the cleaning process the filter be removed from the system.

The water containing the dissolved treatment composition continues circulating through the water system for a period of time to achieve effective cleaning of the water system. The duration of a treatment cycle will depend on factors such as the concentration of the active components of the treatment composition in the water system, the specific surfactant used, the flow rate of water through the system, and the degree or level of materials that need to be cleaned from the system, as will be understood by those of ordinary skill in the art. With larger circulating systems, such as cooling towers, the treatment cycle is typically 24-48 hours. In boiler system, it is preferable that the treatment composition contact the components of the system for 0.1 to 60 days.

Many of the anthropogenic water systems use materials that can react with the chelating agents, the surfactant, or even the secondary biocide. As such, the system may be monitored for the formation of corrosion and corrosion by-products during treatment. It is preferred that an electrochemical corrosion monitor be used to measure real time corrosion in the system during treatment. Additionally, a corrosion rack containing coupons of the reactive metals in the system may be used to monitor the corrosion rates within the water system. The presence of the corrosion inhibitors should prevent many of the critical components of the system from being attacked. The range of concentrations for the active components of the treatment composition according to the invention should have minimal corrosive impact on the water system when used with suitable corrosion inhibitors; however, concentrations of active components of the treatment composition that are above the upper limit of the range (more than 10× the minimum values of 1350 neutral salt, 60 ppm acid salt, and 100 ppm surfactant (for quat or 268 ppm for Aerosol OS) may result in unacceptably high corrosion rates for long term treatment. At such high concentrations, the corrosion rates on mild steel, galvanized steel, and copper after 24 hours of treatment may be up to an order of magnitude higher than the acceptable limits. Additionally, these higher concentrations in the presence of galvanized steel in high laminar flow environments have been shown to produce a waxy coating that comprised the surfactant and the chelating chemicals. However, when using the treatment composition according to the invention at the minimum concentration values, the corrosion rates on mild steel should be within acceptable limits and even lower than with other prior art treatment compositions.

Many flowing water treatment systems use increasing conductivity (resulting from increased metal ion and carbonate concentration as the water is cycled) as an indicator to trigger bleed off water and add fresh water. This practice helps prevent and slow down the formation of hard scale in the system. When the treatment composition is fully added to the water system according to the invention, the conductivity of the water will typically increase by 800 µS or 900 µS. This increase is normally sufficient to trigger the water system to bleed water to the drain, which would result in wasting the treatment composition before it has sufficient time to circulate through the water system for an effective treatment period. Therefore prior to adding any treatment composition to the water system, it is preferred to disable the bleeding mechanism for the system to prevent pre-mature discharge of the treatment chemicals.

Other treatment compositions, such as biocides and corrosion inhibitors, may be used during normal operations; however, it is preferred to periodically repeat the treatment method of the invention to thoroughly clean the water system as it has been found that even water systems appearing to be clean contain microorganisms, algae, and biofilms that are removed by the treatment composition and method of the invention.

Those of ordinary skill in the art will also appreciate upon reading this specification, that modifications and alterations to the composition and methodology and system for using the composition may be made within the scope of the invention and it is intended that the scope of the invention disclosed herein be limited only by the broadest interpretation of the appended claims to which the inventor is legally entitled.

We claim:

1. A solid amine salt composition for treating a boiler or heated water system, the composition comprising cyclohexylamine and morpholine, at least one sulfite, and at least one phosphate, and water;
    wherein the cyclohexylamine and morpholine combined comprise around 30% to 70% of the composition by weight; and
    wherein the sulfite or sulfites combined comprise around 0% to 40% of the composition by weight.

2. The solid composition according to claim 1 comprising around 0% to 30% of the sulfite.

3. A method of treating a boiler or heated water system, the method comprising the steps of:
    providing a solid amine salt treatment composition comprising a cyclohexylamine and morpholine, at least one sulfite, and at least one phosphate; and
    contacting the water containing the treatment composition with components of the boiler or heated water system being treated for a period of time;
    wherein the cyclohexylamine and morpholine combined comprise around 30% to 70% of the composition by weight; and
    wherein the sulfite or sulfites combined comprise around 0% to 40% of the composition by weight.

4. The method of claim 3 wherein the solid composition is an amine salt comprising about 20% to about 30% cyclohexylamine and about 10% to 20% morpholine, about 5% to 40% total weight of one or more phosphates, about 0 to 30% total weight of one or more sulfites, and 3 to 10% water.

5. The method of claim 3 wherein the amine salt comprises about 30% to 40% sodium metabisulfite.

6. The method of claim 5 wherein the amine salt comprises about 15% to 30% monosodium phosphate.

7. The method of claim 3 further comprising dissolving the solid treatment composition in a dissolution chamber to form a concentrated liquid at the treatment site, and feeding the concentrated liquid into the boiler or heated water system being treated.

8. The solid composition of claim 2 wherein the phosphate is monosodium phosphate, disodium phosphate, trisodium phosphate or a combination thereof and the sulfite is sodium metabisulfite, or sodium sulfite, or both.

9. The solid composition according to claim 2 wherein the composition comprises around 20% to 30% cyclohexylamine and around 10% to 20% morpholine.

10. The solid composition according to claim 9 wherein the composition comprises around 20% to 25% cyclohexylamine and around 15% to 20% morpholine.

11. The solid composition according to claim 10 wherein the composition comprises around 10% to 30% total of the phosphate or phosphates.

12. The solid composition according to claim 1 comprising around 30% to 40% sodium metabisulfite and around 15% to 30% total of the phosphate or phosphates.

13. The solid composition according to claim 12 wherein the composition comprises around 20% to 25% cyclohexylamine and around 15% to 20% morpholine.

14. The method according to claim 6 wherein the amine salt comprises about 20% to 25% cyclohexylamine and about 15% to 20% morpholine.

15. The method of claim 4 wherein the amine salt comprises about 15% to 30% monosodium phosphate.

16. The method according to claim 15 wherein the amine salt comprises about 20% to 25% cyclohexylamine and about 15% to 20% morpholine.

17. A solid amine salt composition for treating a boiler or heated water system, the composition consisting essentially of:
    30%-70% total weight of cyclohexylamine and morpholine;
    10-40% total weight of sodium sulfite, sodium metabisulfite, or both;
    15%-30% total weight of one or more phosphates;
    3%-10% water; and
    a conditioning agent to aid in forming the composition into tablets or pellets.

18. The solid amine salt composition according to claim 17 wherein the cyclohexylamine is 20% to 25% by weight of the composition and the morpholine is 15% to 20% by weight of the composition.

19. The solid amine salt composition according to claim 18 wherein total weight of sulfites is 10-30%.

20. A solid amine salt composition for treating a boiler or heated water system, the composition comprising around 20% to 30% by weight cyclohexylamine, around 10%-20% by weight morpholine, around 2% to 70% of one or more phosphates, and wherein the composition does not include sulfites.

21. The solid composition according to claim 20 wherein the composition comprises about 20% to 25% cyclohexylamine, about 15% to 20% morpholine.

* * * * *